United States Patent [19]
Crosby

[11] 3,960,540
[45] June 1, 1976

[54] GROWTH REGULATION IN LAWN CARE

[75] Inventor: Wayne Howard Crosby, Irvington, N.Y.

[73] Assignee: General Foods Corporation, White Plains, N.Y.

[22] Filed: Dec. 23, 1974

[21] Appl. No.: 535,472

Related U.S. Application Data

[63] Continuation-in-part of Ser. No. 265,077, June 21, 1972, abandoned, which is a continuation-in-part of Ser. No. 216,833, Jan. 10, 1972, abandoned.

[52] U.S. Cl. .................................. 71/76; 71/86; 71/103
[51] Int. Cl.$^2$............................................ A01N 5/00
[58] Field of Search....................... 71/76, 86, 103

[56] References Cited
UNITED STATES PATENTS

| | | | |
|---|---|---|---|
| 3,462,257 | 8/1969 | McVey et al. | 71/76 |
| 3,639,474 | 2/1972 | Harrington et al. | 71/103 |

FOREIGN PATENTS OR APPLICATIONS

| | | | |
|---|---|---|---|
| 803,947 | 1/1969 | Canada | 71/86 |

OTHER PUBLICATIONS

Karchi, "Effect of Ethel as Composed to that of CCC etc.", (1969), CA 72, No. 110059v. (1970).

Van Andel, "Dual Effect of 2-Chloroethanephosphonic etc.," (1970) CA 73, No. 119498r. (1970).

*Primary Examiner*—Glennon H. Hollrah
*Attorney, Agent, or Firm*—Doris M. Bennett

[57] ABSTRACT

The combination of 2-chloroethylphosphonic acid and one or more chemical inhibitors of plant growth such as 3-trichloromethylsulfonamido-p-acetotoluidide or a water soluble salt thereof alters the morphology and growth pattern of non-tropical turf grasses when applied thereto, resulting in healthy turf grasses which exhibit predominant lateral growth and suppressed vertical growth. The coordinating combination of the two growth regulating agents is most effective when applied as an aqueous mixture containing a small amount of surfactant.

The growth regulating agent can be applied as an aqueous spray or foam, or as a dry application. They can also be included in a complete fertilizer system which can be applied in liquid or dry form.

3 Claims, No Drawings

GROWTH REGULATION IN LAWN CARE

This application is a continuation-in-part of application Ser. No. 265,077 filed June 21, 1972 now abandoned, said latter application being a continuation-in-part of application Ser. No. 216, 833 filed Jan. 10, 1972, now abandoned.

BACKGROUND OF THE INVENTION

This invention relates, in general, to plant growth regulation, especially to horticultural plant growth regulation and, in particular, is directed to chemical compositions for regulating the growth of turf grasses.

The maintenance of established lawns may involve the application of fertilizer two or three times a year, usually during the growing season, and frequent mowing of the grass. In general, the healthier the lawn grasses, the faster the growth and the more frequently the grass must be cut in order to retain its healthy condition and attractive appearance. Thus, the typical home owner is confronted with the time consuming and, at times, arduous task of mowing the lawn at least once and usually twice every ten days during the growing season. During ideal weather conditions, including plentiful rainfall, the grass may have to be mowed even more frequently in order to maintain its vigorous condition and presentable appearance.

The prior art has long recognized the need for a practical method for inhibiting the vertical growth of turf grasses without impairing the general health of the grass. Still more desirably, there has been a long felt need for a growth regulating composition which is capable of effecting a reduction in vertical growth, while at the same time, promoting lateral growth. Although many chemical agents have previously been suggested for application to lawns for this two-fold purpose, that is, of regulating the vertical and horizontal growth of grass while not impairing the general health thereof, no known growth regulator or combination thereof has apparently been successful in attaining this two-fold goal.

Maleic hydrazide has been reported as early as 1949 to have the capability of inhibiting the growth of plants without killing them. It is reported to act as a mytotic poison and, as such, to stop normal cell division in susceptible plants. Accurate dosage of maleic hydrazide has been determined to be very critical and, since broadleaf plants are less affected by the compound, one or two applications of a slight overdose usually results in the lawn grasses tending to die and the weedy species to predominate; for these reasons, it is seldom used to retard the growth of fine turf grasses.

In the early 1960's, a group of chlorinated and fluorinated carboxylic acid compounds was determined to cause morphological changes in plants. These compounds bring about morphological changes in plants considerably more slowly and with a lack of persistence compared with other synthetic regulators such as maleic hydrazide and are given the characterizing group designation of "Morphactins." The methyl esters of three of the compounds —methyl-2-chloro-9-hydroxy-fluorine-9-carboxylate, methyl-9-hydroxy-fluorine-9-carboxylate, and methyl-2, 7-dichloro-9-hyroxyfluorine-9-carboxylate— are currently employed in combination as the active plant growth regulating ingredients in a commercial formulation to control seed head formation in weedy annual bluegrass and, in combination with maleic hydrazide, are suggested as growth retarding agents for turf grasses and weeds, primarily for roadside and golf course maintenance.

In 1969, McVey (U.S. Pat. No. 3,462,257) disclosed the use of 6-azauracil in combination with a nitrogen-containing fertilizer and other essential plant nutrients as a plant growth regulating composition for effectively retarding the growth of turf species. Since the azauracils are chemical analogs of the nucleic acid constituents, thymine and uracil, they quite possibly inhibit the growth of turf grasses by interfering with the replication of nucleic acids. As such, they may also have similar negative effects in animals, and thus, may be potentially hazardous to humans and pets during and after applications to lawns.

More recently, Harrington et al., in U.S. Pat. No. 3,639,474 have disclosed 5-acetamido-2-methyltrifluoromethanesulfonanilide, also termed 3-trifluoromethylsulfonamido-p-acetotoluidide, as being particularly active in the control of tobacco suckers and retardation of growth of some plants, including grass species, without significant distortion of the normal foliar shape. The 3M Company, St. Paul, Minn., assignee of the patent, has marketed 3, trifluoromethylsulfonamido-p-acetotoluidide in a diethanolamine salt form under the name of "Sustar". According to the 3M Company, several turf grasses have exhibited excellent vegetative growth inhibition and seed head suppression, after application of "Sustar" at the recommended rates. Occasional slight discoloration of short duration has also been evident and top growth inhibition lasting from four to six weeks has been induced from a single application.

Also in 1969, Fritz et al. patented (Canada No. 803,947) a plant growth regulation process utilizing phosphoric compounds. Amchem Products, Inc., Ambler, Pennsylvania, the assignee of the patent, has commercialized at least one of the phosphoric compounds; namely, 2-chloroethyl-phosphonic acid under the trade name "Ethrel" known otherwise as ethephon. According to the patent, many of the phosphonic compounds, including 2-chloroethyl-phosphonic acid (Ethrel) have demonstrated commercial use and growth regulating properties including the inducement of sprouting of underground buds of monocotyledonous plants and, in many cases, growth stimulation at one or more of the customary growth sites to affect increase yields of fruit by control of apical dominance.

Although many investigations have been made toward the development of the vertical growth inhibitors for turf grasses, apparently none of the products from these inventigations has met with wide consumer acceptance for use on residential lawns and none is known to be presently commercially available for such purpose. The present invention is, therefore, directed to an improved and comparatively safe and reliable method for inhibiting the vertical growth of turf grasses and promoting the lateral growth of the same without impairing the health of the grass; that is, without substantially affecting the color of the grass or the appearance of the blade itself. This invention makes possible a significant reduction in the frequency of mowing necessary to maintain turf grasses in a healthy and attractive appearing condition. As such, the invention has provided a satisfactory solution to the heretofore long felt but unresolved need for safe, effective, and reliable growth-regulating agents for turf grasses capable of maintaining at the same time, the healthy appearance of the grasses.

SUMMARY OF THE INVENTION

An important object of the present invention is to provide a chemical composition which, when applied to turf grasses according to the method of the invention, will inhibit the vertical growth and promote the lateral growth of turf grass while, importantly, having no appreciably deleterious effect on the external appearance of the turf grass itself. This is achieved by employing a combination of specific growth regulators which when present at defined ratios may be applied at a cumulative dosage level surprisingly without adversely affecting the health of the grass. Equivalent levels of only one component of this invention cannot be applied without permanent damage to the grass and significant stem elongation.

It is another object of the invention to provide a chemical agent which has a wide dosage tolerance for affecting inhibition of turf grass vertical growth without impairing the health of the grass.

It is still another object of the invention to provide a plant growth regulating agent which is effective when applied to lawn grasses before, after, or in combination with typical lawn grass fertilizers.

It is a feature of the invention that the plant growth regulating composition can be advantageously and effectively applied to turf grasses as the active composition in a foliar spray or with a foam-producing carrier.

Advantageously, the plant growth regulating composition of the invention is effective in limited quantities and is rapidly assimilated by the turf, leaving little, or no residue to potentially harm birds, pets, or humans. A further advantage of the plant growth regulating composition of the invention resides in the fact that it can act as a systemic agent and can be applied directly to the plant stems, leaves and roots to effect the stimultaneous suppression of the vertical growth and stimulation of the lateral growth of many types of lawn grasses.

Briefly, the above mentioned objects, features, and advantages of the present invention are attained by the concurrent use of 2-chloroethyl-phosphonic acid (Ethrel) in combination with 3-trifluoromethylsulfonamido-p-acetotoluidide (Sustar). This novel combination of chemicals when employed together at a specific ratio range and at a specific concentration per acre has the unique capability of inhibiting the vertical growth of turf grasses, promoting the lateral growth of the grass plants, and contemporaneously having no long-lasting adverse effect on the external appearance of the grass in terms of appreciably causing a change in the color of the blades or of the general appearance of the turf.

Surprisingly, it has been discovered that 2-chloroethylphosphonic acid (Ethrel) which has heretofore been employed as a growth regulating agent for fruit and vegetable plants and most recently was found to cause reduction of leaf size and internode elongation in the main shoots of Kentucky bluegrass can, in the presence of a chemical agent for inhibiting the vertical growth of grass, promote the growth of grass tillers and rhizomes. The discovery is all the more surprising in that the activity of "Ethrel" compliments and augments synergistically the activity of 3-trichloromethylsulfonamido-p-acetotoluidide (Sustar) to selectively inhibit the vertical growth of the grass blades while the growth of the grass tillers and rhizomes remains appreciably unaffected.

What has apparently escaped the prior art and that which is the nub of the invention is the discovery that a growth regulating agent, other than a fertilizer, which promotes the growth of tillers and rhizomes can be combined with a second type of growth regulating agent which inhibits grass blade growth to provide a composition which produces a significant reduction of grass vertical growth, a reduction of seed head formation, and the stimulation of lateral development of the turf grass by the enhancement of the growth of tillers and rhizomes. During this time, the desirable green color, relatively wide blade and absence of brown tip characteristics are surprisingly retained since equivalent total dosage levels of any of these components employed separately often results in permanent chlorosis, significant stem elongation and narrowing of the grass blade itself.

In effect, the invention comprehends the application of a specific combination of plant growth regulating agents at specific concentrations to alter the growth pattern of turf grasses so as to significantly shift the growth and production of flowers, seed heads and elongated leaf blades to the production of short thick plants having many tillers at their bases. Surprisingly, this effect has been obtained only by employing "Ethrel" and "Sustar" at the specific proportions later to be discussed.

The prior art has been cognizant of the fact that the application of these plant growth regulating agents designated for inhibiting the vertical growth of grass blades will, especially upon repeated applications, tend to impair the overall health of the grass and, if the applications are excessive, can kill the plants. The deleterious effects of these agents can, to some extent, be compensated by the application of fertilizer and other nutrients. However, fertilizers are apparently nonselective in promoting growth and will encourage the vertical regrowth of the plant blade and thus offset the activity of the plant growth inhibiting agent. The use of a fertilizer will, therefore, require repeated and, in some instances, larger dosages of inhibiting agents. In many respects, the plant is being subjected to two opposing forces, and unless a precise balance is carefully maintained, failure will often result.

In contradistinction to the combination of a fertilizer and a plant growth regulating agent for inhibiting the vertical growth of grass plants, it is theorized that "Ethrel," in addition to selectively promoting lateral growth of the grass plant, synergistically with "Sustar," inhibits the vertical growth of the grass plant. That is, "Ethrel" stimulates the promotion of tillers and rhizomes, and collaterally augments the activity of the plant growth regulating agent to inhibit vertical growth. Thus, less plant growth regulating agent is required to effect the desired inhibition and the danger of impairing the health of the grass is, therefore, greatly lessened. Equally important, the activity of conventional fertilizer is compatible with the "Ethrel" activity and the supply of nutrient appears to be directed predominantly toward the production of more tillers and rhizomes rather than toward the production of elongated blades.

The features of this invention which are believed to be novel are set forth with particularity and distinctly claimed in the concluding portion of this specification. The invention, however, both as to its organization and operation, may best be appreciated by reference to the following detailed description of the preferred embodiments.

DESCRIPTION OF THE INVENTION

The present invention encompasses a plant growth regulating composition comprised of at least two chemical agents, 2-chloroethyl-phosphonic acid, hereinafter referred to as "Ethrel" and 3-trichloromethyl-sulfonamido-p-acetotoluidide, hereinafter referred to as "Sustar." "Ethrel" is known to cause significant changes in the growth and development of many plants including the stimulation of the production of tillers in grasses. Ethrel is available as the active ingredient in several formulations developed by the Amchem Products Division of Rorer-Amchem Corporation, Fort Washington, Pa. The acid form is a very hygroscopic white crystalline material with a melting point of 74°–75°C and molecular weight of 144.5. It is very soluble in water, alcohol, acetone, propylene glycol and other polar solvents, and only slightly soluble in non-polar solvents such as benzene or toluene. It forms mono-and di-esters with simple alcohols such as methanol and ethanol, as well as with aromatic hydroxy compounds such as phenol. It is stable in aqueous solutions below a pH of 3.5. As the pH rises above 3.5 in the presence of free water, hydrolysis of the molecule takes place slowly and releases ethylene gas, chloride and phosphate ions. The rate of hydrolysis appears to be related to the alkalinity of the solution—the higher the pH, the more rapid the hydrolysis. It is believed that the ethylene released Ethrel at a pH of 3.5 or above, is the agent which most influences the morphological change in the turf grasses toward the development of tillers and rhizomes.

To insure stability, Ethrel is dissolved in a propylene glycol base. A standardized concentration of two pounds of Ethrel dissolved in propylene glycol to make one gallon of solution is the preferred medium for employing the compound in the inventive combinations of plant growth regulating agents.

It should be emphasized that the immediate invention is intended to cover only temperate turf grasses since those growing in tropical environments have different growth patterns. Therefore, whether the composition of the immediate invention would function thereon cannot reasonably be foreseen.

Examples of the grasses to which this invention finds application are therefore, the common (unnamed) Kentucky Bluegrasses, as well as the well-known varieties such as Merion, Windsor, Delta and Fylking; perennial Rye grasses such as Manhattan Rye grass; Creeping Red Fescue; Dutch White Clover; and the like.

EXAMPLE I

USE OF ETHREL - SUSTAR COMBINATION TO REGULATE THE GROWTH OF TURF GRASSES

Small scale experiments were designed to treat contiguous ten square foot plots of turf grass grown under similar conditions of fertilization, watering, and maintenance. The plots of grasses included those of Marion and Windsor Kentucky Bluegrasses and Common (unnamed) Kentucky bluegrasses which had been fertilized with a complete lawn fertilizer and mowed to a height of five centimeters two days prior to the application of the agents. 2.0 ml of Ethrel propylene glycol base solution and a concentration of 2 pounds of the acid per gallon (obtained from Amchem Corp., Fort Washington, Pa. and identified as Ethrel No. 68–240).

The mixture was shaken vigorously to disperse the agents and the cloudy flocculation which appeared upon the addition of the Ethrel solution was quickly dispersed by the shaking. Sufficient distilled water was then added to bring the total volume of the aqueous mixture of 120 mls.

a. Application of the growth regulating agent combination to the turf — The aqueous mixture was applied to the turf grasses with a small hand-operated piston type sprayer. The mixture of Ethrel and Sustar was uniformly sprayed onto the foliage of the grass in the identified 2 ft. by 5 ft. plots at a dosage level of 12 ml/ft.$^2$ of aqueous mixture— equivalent to approximately 140 gals. per acre of turf area and corresponding to an application level of 5 lbs. of the active ingredients per acre at a ratio of 2 parts of Ethrel to 1 part of Sustar. Application was made for all of the test plots either early in the morning or late in the afternoon in order to minimize the rate of evaporation and made only on days on which no rain was forecast for at least 24 hours.

b. Observations And Results — Measurements of both the height and color of the grass were made at weekly intervals for six weeks after the application. Growth continued at its normal rate for most of the first week, and then the vertical growth of the blades of grass slowed significantly to about fifty percent of the control plots. Between three to five weeks after the application, the lateral growth of the grasses had visibly increased due to the more horizontal position of the blades and an increase in production of tillers. The significant reduction in vertical growth lasted for approximately six weeks. The plot was then mowed and a second application was made. Six weeks after the second application, the results were substantially the same as after the first application.

EXAMPLE II

USE OF ETHREL PLUS SUSTAR IN A FOAM CARRIER TO REGULATE THE GROWTH OF TURF GRASSES

The combination of Ethrel and Sustar was formulated with a foam-providing concentrate and applied to an experimental 50 ft.$^2$ plot of Common Kentucky bluegrass as the active growth regulating agents in a high expansion foam layer.

a. Preparation Of The Application Mixture—

Approximately 200 ml of a foam-producing concentrate containing the combination of Ethrel and Sustar was formulated as follows:

| INGREDIENTS | PERCENT BY WEIGHT |
| --- | --- |
| Sodium lauryl sulfate (1) | 19.5 |
| Blended alkyl sulfates (2) | 17.2 |
| Isopropyl alcohol | 33.2 |
| Water | 19.5 |
| Propylene Glycol | 3.7 |
| Glycerol | 5.5 |
| "Ethrel" | 0.9 |
| "Sustar" | 0.5 |
| | 100.00 |

(1) STEPANOL 360 (35% active sodium lauryl sulfate) manufactured by Stepan Chemical Co. Northfield, Illinois.
(2) STEPANOL 317 (92.5% active blend of linear alkyl sulfonates; linear alcohol ether sulfonates derived from such alcohols as lauryl, myristyl, cetyl alcohols, etc. and neutralized with an alkanolamine; and alkylolamides) manufactured by Stepan Chemical Co., Northfield, Illionis.

The ingredients were added to the water and stirred to form a homogeneous fluid. No flocculations or precipitation was observed either at the time of addition or during a two week storage period.

b. Application Of The Growth Regulating Agent Combination To The Turf — The combination of Ethrel and Sustar was applied to the 50 ft.$^2$ test plot of Kentucky bluegrass incorporated on a high-expansion foam. An experimental water-operated hose-end foaming unit was employed to generate the foam. In order to apply the agents uniformly to the 50 ft.$^2$ plot, the mixture was educted at a rate of 3 parts of concentrate to 97 parts of water from a garden hose, and sprayed onto the screen of the foam generating unit to form a highexpansion foam. This foam which contained the growth regulating agents, was then applied uniformly to the area of grasses bounded by a 5 ft. × 10 ft. wood frame. It took approximately 40 seconds to cover the grass foliage with a blanket of foam averaging 3 inches thick. The foam blanket slowly broke down, depositing the active ingredients on the blades of grass. No discoloration was observed on the Kentucky bluegrass treated with these agents applied as a foam. This dosage was equivalent to four pounds of active ingredients (a.i.)/acre of Ethrel plus 2 pounds a.i./acre of Sustar. The reduced rate of growth was evident after one week, and continued for approximately six weeks. The rate of growth was about half that observed in the untreated control plots.

The following representative data are presented to demonstrate the effectiveness of the inventive combinations to regulate the growth of turf grasses. The data also illustrates the significant benefits obtained by the inventive combination as contrasted to untreated turf and to the use of either agent of the combination singly. The ratio of weights in agents employed and of dosages applied to the grass are indicative of the best modes of practicing this invention.

EXAMPLE III

An aqueous solution of 1 part by weight of Sustar and from one to two parts by weight of Ethrel was prepared. The effects of the specific combinations of Ethrel and Sustar were evaluated on flats of Kentucky Bluegrass, variety Fylking, after three weeks under greenhouse conditions.

TABLE I

INHIBITION OF GROWTH OF FYLKING KENTUCKY BLUEGRASS AT 3 WEEKS AFTER FOLIAR APPLICATION IN GREENHOUSE

| Agent | Dosage (lbs/Acre) | % Growth Inhibition |
|---|---|---|
| Water Control | 5 | 0 |
| Ethrel | 3 | 21 |
| Sustar | 2 | 8 |
| Ethrel | 2 | 11 |
| Ethrel & Sustar | 3 / 2 | 46 |
| Ethrel & Sustar | 2 / 2 | 38 |

Note that in the application of 3 Ethrel/2 Sustar, one would expect a cumulative % growth inhibition of about 29% (21+8). However, a synergestic 46% growth inhibition was obtained. Similarly, in the case of 2 Ethrel/2 Sustar, where one would expect 19% growth inhibition (11+8) a 38% reduction in growth was obtained.

EXAMPLE IV

An aqueous solution of 1 part by weight of Sustar and from one to two parts by weight of Ethrel was prepared, which solution contained in addition a surfactant, specifically at a concentration of 36 percent by weight of the growth regulating compositions. The effects of the specific combinations of Ethrel and Sustar were evaluated on Kentucky Bluegrass, variety Fylking, after four and five week periods in terms of color evaluation, growth patterns and percent growth inhibition, the results of that evaluation being set forth in Tables 1, 2, and 3.

TABLE I

INHIBITION OF GROWTH OF FYLKING KENTUCKY BLUEGRASS AT 4 WEEKS AFTER FOLIAR APPLICATION

| AGENT | DOSAGE IN LBS/ACRE | TURF APPEARANCE | % GROWTH INHIBITION |
|---|---|---|---|
| Water Control | — | Normal appearance and normal color | 0% |
| Ethrel | 2 | Darker than normal | 11% |
| Ethrel | 3 | Darker than normal some stem elongation | 18% |
| Ethrel | 4 | Darker than normal some stem elongation and matting | 42% |
| Ethrel | 5 | Very dark, significant stem elongation and matting | 33% |
| Sustar | 2 | Normal appearance and normal color | 7% |
| Sustar | 4 | Brown tips and some thatching | 31% |
| Sustar | 5 | Dull green wih brown tips | 37% |
| Ethrel & Sustar | 2 / 2 | Normal color, wide blades, normal stems | 43% |
| Ethrel & Sustar | 3 / 2 | Dark green color, wide blades, normal stems. | 44% |

TABLE II

NEGATIVE SIDE- EFFECTS OF GROWTH REGULATORS ON FYLKING KENTUCKY BLUEGRASS AT 4 WEEKS AFTER FOLIAR APPLICATION

| AGENTS | DOSAGE IN LBS/ACRE | % GROWTH INHIBITION | NEGATIVE EFFECTS |
|---|---|---|---|
| Ethrel | 4 | 42% | elongated stems, matted appearance |
| Sustar | 4 | 31% | brown tips, thin sparse appearance |
| Ethrel | 3 | 18% | slight elongation at the stems |
| Ethrel | 5 | 33% | stem elongation and matted appearance |
| Sustar | 5 | 37% | brown tips, sparse |
| Ethrel & Sustar | 2 / 2 | 43% | None |

TABLE III

APPEARANCE OF FYLKING BLUEGRASS AT FIVE WEEKS AFTER SPRAY APPLICATION OF GROWTH REGULATING AGENTS

| AGENT | PERCENT GROWTH INHIBITION | COLOR | MORE TILLERS | STEM ELONGATION | LEAF TIP COLOR | DENSITY |
|---|---|---|---|---|---|---|
| Ethrel | 18 | Normal | Yes | Significant | Normal | Normal |

TABLE III-continued

APPEARANCE OF FYLKING BLUEGRASS AT FIVE WEEKS AFTER SPRAY APPLICATION OF GROWTH REGULATING AGENTS

| AGENT | PERCENT GROWTH INHIBITION | COLOR | MORE TILLERS | STEM ELONGATION | LEAF TIP COLOR | DENSITY |
|---|---|---|---|---|---|---|
| (3 lbs/acre) Ethrel (5 lbs/acre) | 33 | Dark | Yes | Significant | Normal | Thick and Matted |
| Sustar (2 lbs/acre) | 7 | Normal | No | None | Normal | Normal |
| Sustar (5 lbs/acre) | 27 | Dull | No | None | Brown | Sparse Thin |
| Ethrel & (3 lbs/acre) Sustar (2 lbs/acre) | 34 | Normal | Yes | Slight | Normal | Normal Appearance With More Tillers |

Basis the result set forth in Tables 1, 2, and 3, it is evident that the combination of 1 part Sustar to 1 to 2 parts Ethrel to give a final concentration of between four and six pounds of growth regulator per acre results in a percent growth inhibition which is greater than the percent growth inhibition which is expected from the aggregate of equivalent levels of the same growth inhibitors when the respective levels of each are used separately. Most significantly, however, the combination of Sustar and Ethrel in the aforementioned ratio range when applied to grasses at a concentration of four to six pounds per acre eliminates the negative characteristics imparted to grasses when four to six pounds of only Ethrel or only Sustar are applied alone, a result which could not have been anticipated on the basis of the prior art's disclosure of combinations of other known growth regulators.

Without further analysis, the foregoing will so reveal the gist of the present invention that others can, by applying current knowledge, readily adapt it for various applications without omitting features that, from the standpoint of prior art, fairly constitute essential characteristics of the generic and specific aspects of the invention.

What is claimed is:

1. A composition of synergistically inhibiting the vertical growth of temperate turf grasses and concomitantly promoting the lateral growth of said grasses which consists essentially of a uniform blend of:
   a. about 2 parts by weight of 3-trichloromethyl sulfonamido-p-acetotoluidide, and
   b. about 3 parts by weight of 2-chloroethyl phosphonic acid, said blend incorporated in a quantity of inert carrier sufficient to effect dispersibility in application of the blend to said temperature turf grasses at a dosage level equivalent to about five pounds of blend of active ingredients per acre, said blend having no appreciable deleterious effect on the natural texture and appearance of said grasses.

2. The composition of claim one further including a surfactant in an amount sufficient to effectively promote uniform coverage of the foliage of said temperature turf grasses when applying the composition thereto.

3. A process for altering the morphology and growth pattern of temperate turf grasses without adversely affecting their natural texture and appearance which consists of applying to the temperate turf grass blades a blend of about 2 parts 3-trichloromethylsulfonamido-p-acetotoluidide and about 3 parts 2-chloroethyl phosphonic acid in an amount effective to synergistically inhibit the vertical growth of the turf grass and to concomitantly promote the lateral growth of said grass, said blend incorporated in a quantity of inert carrier sufficient to insure uniform contact of the grass plants with the blend, said blend to be applied at a total dosage level equivalent to about 5 pounds of blend per acre of turf grass.

* * * * *